United States Patent [19]

Altshuler

[11] Patent Number: 6,026,828
[45] Date of Patent: Feb. 22, 2000

[54] TOOTHBRUSH

[76] Inventor: Gregory B. Altshuler, 8R Ferbanks Rd., Wilmington, Mass. 01887

[21] Appl. No.: 09/068,257
[22] PCT Filed: Sep. 10, 1996
[86] PCT No.: PCT/RU96/00257
  § 371 Date: May 5, 1998
  § 102(e) Date: May 5, 1998
[87] PCT Pub. No.: WO98/10711
  PCT Pub. Date: Mar. 19, 1998
[51] Int. Cl.[7] .............................. A46B 11/00; A46B 15/00
[52] U.S. Cl. ........................... 132/311; 132/308; 15/22.1; 433/29; 362/109
[58] Field of Search ................................ 132/311, 308, 132/290, 310, 313; 15/22.1, 22.2, 167.1, 167.2; 433/29, 119, 216, 215, 229; 362/109, 32, 253, 804

[56] References Cited

U.S. PATENT DOCUMENTS

| | | | |
|---|---|---|---|
| 3,593,725 | 7/1971 | Ortega | 132/311 |
| 3,667,454 | 6/1972 | Prince | 15/22 |
| 4,333,197 | 6/1982 | Kuris | 15/22 |
| 4,779,173 | 10/1988 | Carr et al. | 362/109 |
| 5,030,090 | 7/1991 | Maeda et al. | 433/29 |
| 5,160,194 | 11/1992 | Felman | 362/109 |
| 5,306,143 | 4/1994 | Levy | 433/29 |
| 5,369,831 | 12/1994 | Bock | 15/22 |
| 5,546,624 | 8/1996 | Bock | 15/22.1 |
| 5,658,148 | 8/1997 | Neuberger et al. | 433/215 |

FOREIGN PATENT DOCUMENTS

| | | |
|---|---|---|
| 88120821 | 12/1988 | European Pat. Off. . |
| 749380 | 2/1980 | Russian Federation . |
| 2032365 | 4/1995 | Russian Federation . |
| 2066108 | 9/1996 | Russian Federation . |

OTHER PUBLICATIONS

Altshuler, Grigori B. and Andrey V. Erofeev, "Modern Optics and Dentistry", *Lasers in Dentistry*, Chapter 19, pp. 283–297.

Altshuler, G.B. and V.N. Grisimov, "New Optical Effects in the Human Hard Tooth Tissues", reprinted from *Lasers and Medicine*, SPIE Proc Holography Interferometry Opt Pattern Recognition Biomed, vol. 1353, (1989), pp. 97–102.

Altshuler, Grigory, Vladimir Grisimov, Vladimir Ermolaev and Irena Vityaz, "Human Tooth as Optical Device", reprinted from *Lasers and Medicine*, SPIE Proc Holography Interferometry Opt Pattern Recognition Biomed, vol. 1424, pp. 95–104.

Petrischev, N.N., G.B. Altshuler, L.I. Yantareva and L.A. Ermolaeva, "Report on Low Intensity Laser Radiation Usage in Dentistry", St. Petersburg Pavlov Medical Institute and St. Petersburg State Institute of Fine Mechanics and Optics.

*Primary Examiner*—Gene Mancene
*Assistant Examiner*—Philogene Pedro
*Attorney, Agent, or Firm*—Paul C. Remus, Esquire; Kristin Kohler, Esquire; Devine, Millimet & Branch Professional Association

[57] ABSTRACT

A toothbrush providing a radiation source of selected optical range, having the radiation source built into a cavity in the handpiece of the toothbrush. The brush head may be transparent and the bristles may be transparent. Various combinations of scattering, transparent and reflective properties of the brush head, the type of radiation source, and bristle transparency allows selected influence directly on different field and tissues of the oral cavity. Radiation wavelength is selectable to provide treatment to both the soft tissue of the oral cavity and to the teeth. Selected radiation penetrates the pulp of the tooth to stimulate and enhance calcium transport to the dentine and enamel of the tooth to prevent and treat cavities.

11 Claims, 1 Drawing Sheet

TOOTHBRUSH

BACKGROUND OF THE INVENTION

The invention concerns tooth brushes and can be used in dentistry for profilaxis and treatment of oral diseases.

FIELD OF THE INVENTION

A tooth brush is known, as shown in PCT N90/0906, A61 N1/32, A46 B15/00 date of publication 23.08.90, which is hereby incorporated by reference, comprising an electrode on the handle, the electrode having sharpened edges in the base of the bristles. The electronic circuit providing the conditions of application of bipolar pulse train (especially with 50 Hz frequency) to oral tissues, and an LED indicating the operation of the electronic circuit are mounted inside the brush handle. The main disadvantage of this device is that it only influences gum tissue.

There is also known a tooth brush which is closest to the present invention from the technical point of view as disclosed in (Japan N3-15883, A46 B15/00, A61 N5/06, D01 F8/04 date of publication Apr. 03, 1991), which is hereby incorporated by reference, comprising a handle with built-in power supply heater, and a head with bristles made of special thermoactive material radiating in the far infrared range. The main disadvantage of this device is the absence of radiation providing the profilaxis and treatment influence on both teeth and gum.

Thus there is a need for a toothbrush that provides profilaxis and treatment to both teeth and gums.

SUMMARY OF THE INVENTION

The present invention consists of a tooth brush providing profilaxis and treatment influence on both tooth tissues and soft oral tissues.

The specified problem is solved under the realization of the invention due to achievement of technical results consisting of application of radiation of an optical range that provides antiinflammatory and caries-protective influence on oral tissues as well as stimulating their regeneration by providing radiation that penetrates the enamel, dentine, and pulp of the tooth, thereby enhancing transport of calcium to the dentine and enamel.

The specified technical results of the invention are achieved by a tooth brush comprising a handpiece with a cavity, a brush head with bristles, and built in to the handpiece cavity and electrically connected through a switcher, a radiation source and power supply. The radiation source is a source of radiation of a particular optical range and the brush head is made of transparent material and may be disconnected from the handpiece.

The light source may be a laser diode or light emitting diode.

The light source may also be a filament lamp and the handpiece may be made of color transparent material.

The brush head may contain light scattering materials.

The brush head may also have a reflecting or back scattering coating, with bristles made of transparent material.

The brush head may contain photoluminescent substances, especially dyes.

The physiotherapeutic influence of visible and near UV and IR radiation is well known. At low doses these radiations have a biostimulating action on tissues. The most efficient of these radiations is laser radiation as shown in A. S. Kryuk,, V. A. Mostovnikov, I. V. Khokhlov, N. S. Serdyuchenko. Therapeutic efficiency of low-intensity laser radiation. Minsk: Science & Engineering, 1986. V. E. Illarionov. The principles of laser therapy. M. Published by "RESPECT" of "INOTECH-Progress" Co., which is hereby incorporated by reference.

It has been found that there is antibacterial and antiinflammatory action of UV (330–380 nm), blue (440–450 nm) and green (514–590) nm) radiation. In addition the red (630–640 nm) and near IR (830–1300 nm) radiation also provides profilaxis and caries treating influence.

The profilaxis influence against caries is provided by irradiation of odontoblasts and tooth pulp due to the waveguide effect of light propagation in the enamel prisms and dentinal tubules- see G. B. Altshuler, V. N. Grisimov. "The effect of waveguide light propagation in human tooth". Doklady AN USSR, v.310, N5, pp.1245–1248, 1990; G. B. Altshuler, V. N. Grisimov. "New optical effects in the human hard tooth tissues". Proc. SPIE. Lasers and Medicine, v.1353, pp97–102, 1991, which is herein incorporated by reference. The stimulation of the pulp and dentinal tubules enhances transport of calcium to the enamel.

While the gums are irradiated both antiparadontosis action and penetration of light inside teeth take place. The radiation is most efficient in combination with massage of the gums because pressuring of alive soft tissue causes an increase in its transparency thereby providing for better penetration of the radiation- see G. A. Askaryan "The increasing of transmission of laser and other radiation through the soft turbid physical and biological media". Kvantovaya Electronika, V.9, N7, 1982, pp.1370–1383, which is herein incorporated by reference.

The useful irradiation of a whole oral cavity is provided in the claimed tooth brush due to the presence of a light source connected to an electrical power supply and a transparent brush head which can be made of light scattering material.

The type of light source used is determined by the necessity of application of light with specified spectral parameters, and a dose that is useful for the specified type of hard and soft oral tissues.

More intensive irradiation of teeth and gums are provided with a tooth brush that has transparent bristles and reflecting or back scattering coating of the brush head. The increased irradiation delivered is due to the fact that tooth and gum tissue is not completely transparent and reflects some of the initial radiation. A reflective coating on the brush head of course enables some of the reflected initial radiation to be captured in the brush head and redirected back to the mouth cavity.

Photoluminescent substances, especially dyes, introduced into the brush head can provide practically all the useful spectral range of oral cavity radiation under te influence of a single shortwave, for example, UV or blue light source. The single light source excites the particular photoluminescent material which then releases light of the desired wavelength.

Thus, the invention can provide an inexpensive device which does not require the use of a laser and which can still provide any desired wavelength light.

DETAILED DESCRIPTION OF THE INVENTION

Figure 1:
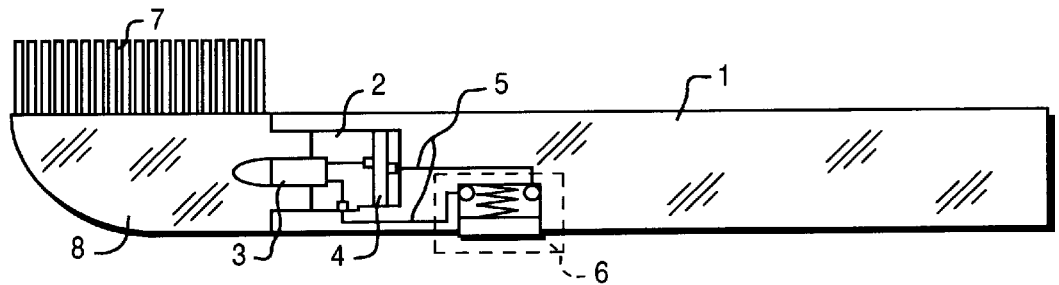
FIG. 1 represents the tooth brush having a radiation source in the form of laser diode or light emitting diode connected to the power supply through the switcher, and having a transparent brush head.
Figure 2:
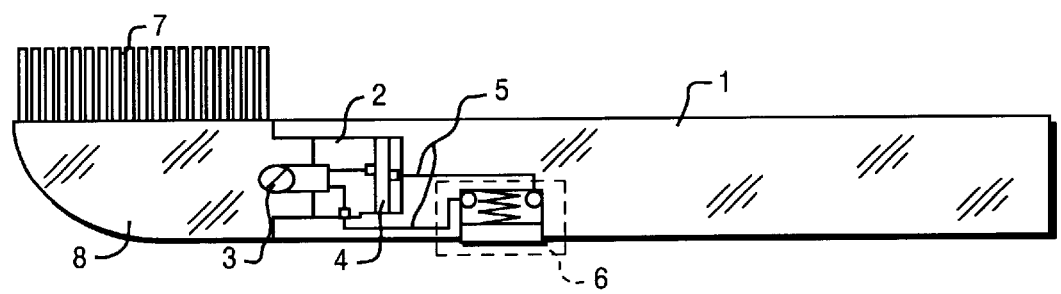
FIG. 2 represents the tooth brush having a radiation source in the form of filament lamp, and a brush head made of color transparent material.

The tooth brush (FIG. 1) comprises a handpiece 1 with cavity 2, a radiation source 3 built-in to handpiece cavity 2 and electrically connected to a power supply 4 through contacts 5 of a switcher 6. The bristles 7 are fixed on a brush head 8, which may be transparent. When a filament lamp is used as a radiation source 3 (FIG. 2) the brush head 8 is made of color transparent material.

Figure 3:
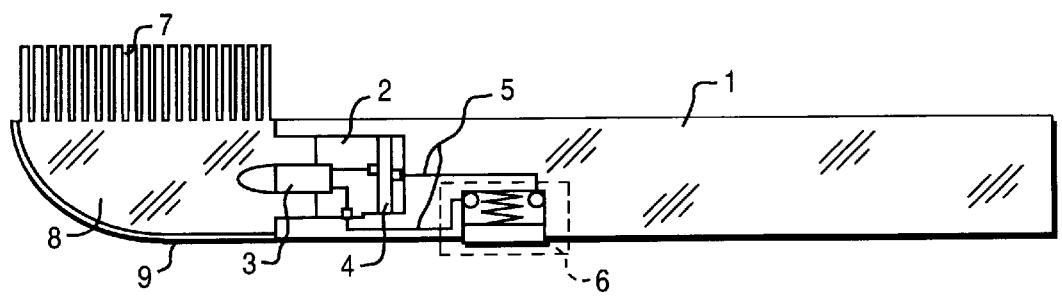
FIG. 3 shows the tooth brush wherein the brush head has a reflecting coating and the bristles are transparent.

The brush head 8 may be covered alternatively by a reflecting coating 9 (FIG. 3) and also may be made of light scattering material and covered by it. When brush head 8 is formed from light scattering material or covered by a reflective coating, the bristles 7 are preferably transparent.

The device operates as follows. After the power supply of radiation source 3 is switched on by pressing a button of switcher 6, the radiation from the source 3 reaches the body of brush head 8 and the oral cavity.

If a filament lamp is used as the radiation source 3, a spectral filter should be used to provide the desired spectral range because of the wide spectral band of the filament lamp source. A brush head made of the desired color (green, blue or red) transparent material may play the role of such filter.

If the bristles 7 are made of transparent material, especially in the case where the brush head 8 is covered by a reflective coating 9, or when the radiation is scattered within the brush head, most of the radiation reaches the bristles, concentrates in them and then reaches the places of contact between bristles 7 and teeth or gum tissues.

Photoluminescent additives, for example dyes, inside the brush head 8 provide irradiation of the oral cavity not only by radiation delivered from the radiation source 3 but also by radiation the spectral parameters of which are defined by Stokes law.

The wavelength of radiation emitted by the photoluminescent substances is always longer than the wavelength of radiation source 3. If there is a single UV or blue radiation source, photoluminescent additives allow one to deliver to the oral cavity the other desirable spectral components of visible and infrared light.

An example device would include the following: laser diodes SDL-2380-S with 810 nm radiation wavelength and SDL-7430 with 675 nm radiation wavelength (see Product Catalog SDL "Semiconductor Diode Lasers" 1995), light emitting diodes are LEDS-5 and LEDS-3 (blue, green, red)(see Catalog "RS components", Viena, 1995), and the low-dimension power supply VARTA chrom 547.

THE INDUSTRIAL APPLICATION

Thus taking into account above the claimed device allows to solve the problem of profilaxis and treatment influence on oral tissues

I claim:

1. A therapeutic tooth brush comprising:

a removable, brush head made of transparent material and having transparent bristles;

a handle with a cavity;

a switch unit;

a light source connected via said switch unit with a power supply which is built in said cavity in said handle;

wherein said light source is a source of radiation of an optical range having a wavelength in the range of about 440–1300 nanometers such that radiation is directable both to the surface of teeth and soft tissues and is directable to penetrate the gum tissue, odontoblasts, and deep within the tooth tissue to stimulate the tooth pulp.

2. The tooth brush as defined in claim 1 wherein said light source is a laser diode.

3. The tooth brush as defined in claim 1 wherein said light source is a light emitting diode.

4. The tooth brush as defined in claim 1 wherein said light source is a filament lamp and said brush head is made of color transparent material.

5. The tooth brush as defined in claim 1 wherein said brush head contains light scattering materials.

6. The tooth brush as defined in claim 1 wherein said brush head has a reflecting or back scattering coating and said bristles are transparent.

7. The tooth brush as defined in claim 1 wherein said brush head contains photoluminescent substances.

8. The tooth brush as defined in claim 1 wherein said light source is located at said brush head, bristles are not present at the point of output of radiation from said brush head and said brush head surface forms an optical lens.

9. The tooth brush as defined in claim 1 wherein material of said brush head is unavailable at the point of radiation output from said brush head.

10. The tooth brush as defined in claim 1 wherein said brush head is mounted with more than one light source.

11. The tooth brush as defined in claim 1 wherein said handle and said brush head are equipped with an electrical connector, wherein one part of said connector is mounted on said brush head and is connected electrically with said light source and another part of said connector is mounted on said brush handle and is connected electrically with said switch unit and said power supply such that said tooth brush is adaptable with respect to said light source.

* * * * *